United States Patent
Horvath

(10) Patent No.: US 9,125,997 B2
(45) Date of Patent: Sep. 8, 2015

(54) PEN NEEDLE HUB HAVING INCREASED CONTACT AREA

(75) Inventor: Joshua D. Horvath, Sparta, NJ (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 12 days.

(21) Appl. No.: 12/205,711

(22) Filed: Sep. 5, 2008

(65) Prior Publication Data

US 2009/0069755 A1 Mar. 12, 2009

Related U.S. Application Data

(60) Provisional application No. 60/935,951, filed on Sep. 7, 2007.

(51) Int. Cl.
*A61M 5/31* (2006.01)
*A61M 5/34* (2006.01)
*A61M 5/32* (2006.01)

(52) U.S. Cl.
CPC ............. *A61M 5/349* (2013.01); *A61M 5/3293* (2013.01)

(58) Field of Classification Search
CPC .............. A61M 5/349; A61M 5/3293; A61M 2005/2418; A61M 5/2033; A61M 5/3202
USPC .................. 604/117, 118, 239, 240
See application file for complete search history.

(56) References Cited

U.S. PATENT DOCUMENTS

| | | | |
|---|---|---|---|
| 2,871,857 A | 2/1959 | Lipari | |
| 4,040,421 A | 8/1977 | Young | |
| 5,611,786 A | 3/1997 | Kirchhofer et al. | |
| 6,843,783 B2 | 1/2005 | Ooyauchi | |
| 6,855,129 B2 | 2/2005 | Jensen | |
| 6,955,660 B2 * | 10/2005 | Fisher | 604/240 |
| 6,986,760 B2 | 1/2006 | Giambattista | |
| 7,077,830 B2 | 7/2006 | Higaki | |
| 2004/0054336 A1 | 3/2004 | Klint | |
| 2004/0186443 A1 | 9/2004 | Covino | |
| 2006/0229562 A1 | 10/2006 | Marsh | |
| 2007/0149924 A1* | 6/2007 | Marsh | 604/117 |
| 2008/0045900 A1* | 2/2008 | Alchas et al. | 604/117 |

FOREIGN PATENT DOCUMENTS

| | | |
|---|---|---|
| EP | 0903156 | 3/1999 |
| GB | 978570 | 12/1964 |
| GB | 1 574 187 | 9/1980 |
| GB | 1574187 | 9/1989 |
| JP | 53-5891 | 1/1978 |
| JP | 04-242663 | 1/1991 |
| JP | 2007503866 | 3/2007 |
| JP | 2007505677 | 3/2007 |
| WO | WO-2007-047403 | 4/2007 |

* cited by examiner

*Primary Examiner* — Bhisma Mehta
*Assistant Examiner* — Brandy S Lee
(74) *Attorney, Agent, or Firm* — Roylance, Abrams, Berdo & Goodman, L.L.P.

(57) ABSTRACT

A pen needle assembly having a hub with an increased surface area that contacts a patient's skin is provided. The increased contact area of the hub with the patient's skin during injection of a cannula decreases the pressure exerted against the patient's skin, thereby increasing the comfort of the patient. A bonding adhesive is disposed on an outer surface of the hub, thereby decreasing the required curing time of the adhesive. Additionally, the increased contact area, between the cannula adhesive and hub increases the strength of the bond therebetween.

17 Claims, 18 Drawing Sheets

PEN NEEDLE HUB HAVING INCREASED CONTACT AREA

CROSS REFERENCE TO RELATED APPLICATION

This application claims the benefit under 35 U.S.C. §119(e) of provisional application Ser. No. 60/935,951, filed Sep. 7, 2007, which is hereby incorporated by reference in its entirety

FIELD OF THE INVENTION

The present invention relates generally to a hub for a pen needle assembly. More particularly, the present invention generally relates to a hub having an increased surface area that contacts a patient's skin during an injection, thereby reducing the pressure exerted against the skin during the injection. Still more particularly, the present invention generally relates to a hub in which the cannula is bonded to the hub by an adhesive disposed on an outer surface of the hub, thereby increasing the strength of the bond, and which is applicable to any number of devices, such as syringes and other needle-containing devices, in which such features are desirable.

BACKGROUND OF THE INVENTION

Insulin and other injectable medications are commonly given with drug delivery pens, whereby a disposable pen needle is attached to facilitate drug container access and allow fluid egress from the container through the needle into the patient.

As technology and competition advance, driving the desire for shorter, thinner, less painful, and more efficacious injections, the design of the pen needle and parts thereof becomes more and more important. Designs need to proactively address ergonomically improving injection technique, injection depth control and accuracy, the ability to be safely used and transported to disposal, and protection against misuse while maintaining the ability to be economically manufactured on a mass production scale.

Drug delivery pens, such as the existing drug delivery pen 100 shown in FIGS. 1 and 2, typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is used by the user to securely hold the pen injector device 100 in a shirt pocket, purse or other suitable location and provide cover/protection from accidental needle injury.

FIG. 2 is an exploded view of the pen needle assembly 100 of FIG. 1. The dose knob/button 24 has a dual purpose and is used both to set the dosage of the medication to be injected and to inject the dosed medicament via the lead screw 7 and stopper 15 through the medicament cartridge 12 attached through the reservoir housing or hub 20. In standard drug delivery pens the dosing and delivery mechanisms are all found within the outer sleeve 13 and are not described in greater detail here as they are understood by those knowledgeable of the prior art. The medicament cartridge 12 is typically attached to a standard pen injector housing via known attachment means, such as ¼ turn fastening features. The distal movement of the plunger or stopper 15 within the medicament cartridge 12 causes medication to be forced into the reservoir housing 20. The medicament cartridge 12 is sealed by septum 16, which is punctured by a septum penetrating needle cannula (not shown) located within hub 20. The hub 20 is preferably screwed onto the medicament cartridge 12, although other attachment means can be used. To protect the patient needle 11, an outer shield 69 attaches to the hub 20. An inner shield 59 covers the patient needle 11 within the outer shield 69. The cap 21 fits snugly against outer sleeve 13 to allow a user to securely carry the drug delivery pen 100.

Another existing pen needle assembly 2 is shown in FIG. 3. The needle assembly 2 includes a cover 101, an inner shield 200, a needle cannula 300, and a needle hub 400. A proximal end 310 of the needle cannula 300 is inserted into a center opening in the distal (patient) end 405 of the needle hub 400 until a predetermined length of the distal end 305 of the needle cannula 300 remains extended. The needle cannula 300 is secured by epoxy or adhesive in the distal end 405 of the hub 400 within the hub protrusion 420.

To protect users from injury and the needle cannula 300 from being damaged, the inner shield 200 covers the exposed portion of needle cannula 300. The open proximal end 210 of the inner shield 200 is placed over the exposed portion of needle cannula 300. The open proximal end 110 of the cover 100 envelops the inner shield 200, needle cannula 300, and hub 400.

Distal end 105 of the cover 101 is closed to prevent contamination and damage to the inner components of pen needle assembly 2, and to prevent injury to anyone who may handle it prior to use. The proximal end 410 of the hub 400 is typically covered by a sanitary cover (not shown) on end 110 of cover 101. The pen needle assembly 2 is then ready for shipment to a user. When the user is ready to use the pen needle assembly 2, the sanitary cover (not shown) is removed, the hub 400 is screwed onto a standard medication cartridge 12 (FIG. 2), and the cover 101 and inner shield 200 are separately removed from the hub 400/cannula 300 subassembly by a pulling action. The distal end 205 of the inner shield 200 is closed to cover the distal end 305 of the needle cannula 300 after the cover 101 is removed to protect the user from an accidental stick. The inner shield 200 is then removed to access the needle cannula 300. Thus, two separate pulling actions are required to remove both the cover 101 and the inner shield 200.

FIG. 4 is a cross-sectional view of a pen needle assembly in the configuration that it would be received by a user (with a sanitary cover not shown). An inner shield 470 covers a needle cannula 430. Additionally, the hub 460 includes a center hub protrusion 465. The skin contact plane 450 is the plane of the straight surface across the distal end of the center hub protrusion 465.

A protrusion 520, in which the cannula is bonded, extending from the hub 500 of existing pen needle assemblies is typically narrow, as shown in FIG. 5. The small surface area 530 provided at the distal end of a narrow hub protrusion 520 results in a high pressure being exerted against a patient's skin during injection of the cannula, thereby increasing discomfort of the patient.

Furthermore, the bonding adhesive used to bond the cannula to the hub is typically disposed within the hub protrusion. The adhesive is cured by exposure to ultraviolet (UV) radiation or by application of heat or chemical reaction from a two-part adhesive. Because the adhesive is within the hub protrusion, the UV radiation must pass through the hub walls, which are typically made of polypropylene, to induce curing in the adhesive. Thus, a lengthy curing time is required to cure the adhesive due to the UV radiation having to pass through the hub walls to irradiate the adhesive.

Drug delivery pens are also disclosed in U.S. Patent Application Publication Nos. 2006/0229562 to Marsh et al. and 2007/0149924 to R. Marsh, the entire contents of both of which are hereby incorporated by reference.

Accordingly, a need exists for a hub protrusion having an increased surface area that contacts a patient's skin during an injection, thereby reducing the pressure exerted against the patient's skin during the injection.

SUMMARY OF THE INVENTION

In accordance with an aspect of the present invention, a hub has an increased surface area that contacts a patient's skin during an injection to reduce the pressure exerted against the patient's skin during the injection, thereby increasing the comfort of the patient.

In accordance with another aspect of the present invention, a bonding adhesive is disposed on an outer surface of the hub, thereby decreasing the required curing time.

In accordance with another aspect of the present invention, the adhesive is disposed on an outer surface of the hub to increase the contact area between the cannula adhesive and hub, thereby increasing the strength of the bond.

Objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying figures, in which.

Throughout the drawings, like reference numbers will be understood to refer to like parts, components and structures.

DETAILED DESCRIPTION OF THE EXEMPLARY EMBODIMENTS

Figure 1:
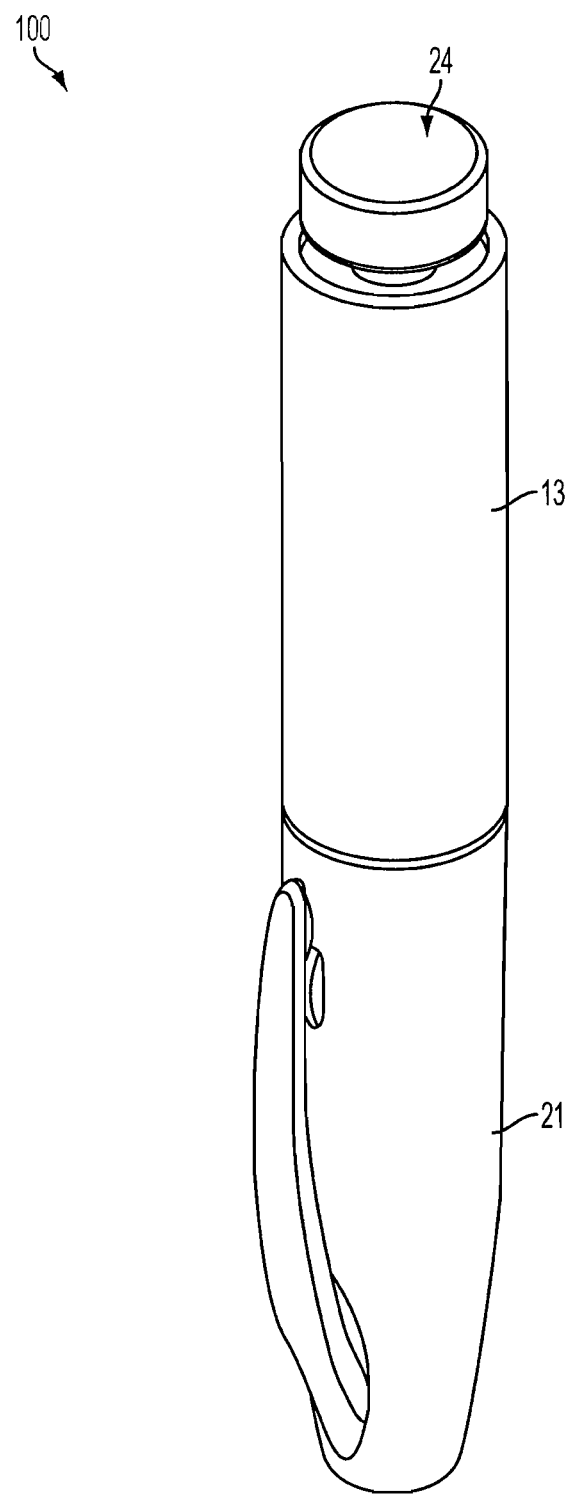
FIG. 1 is a perspective view of an assembled existing drug delivery pen.
Figure 2:
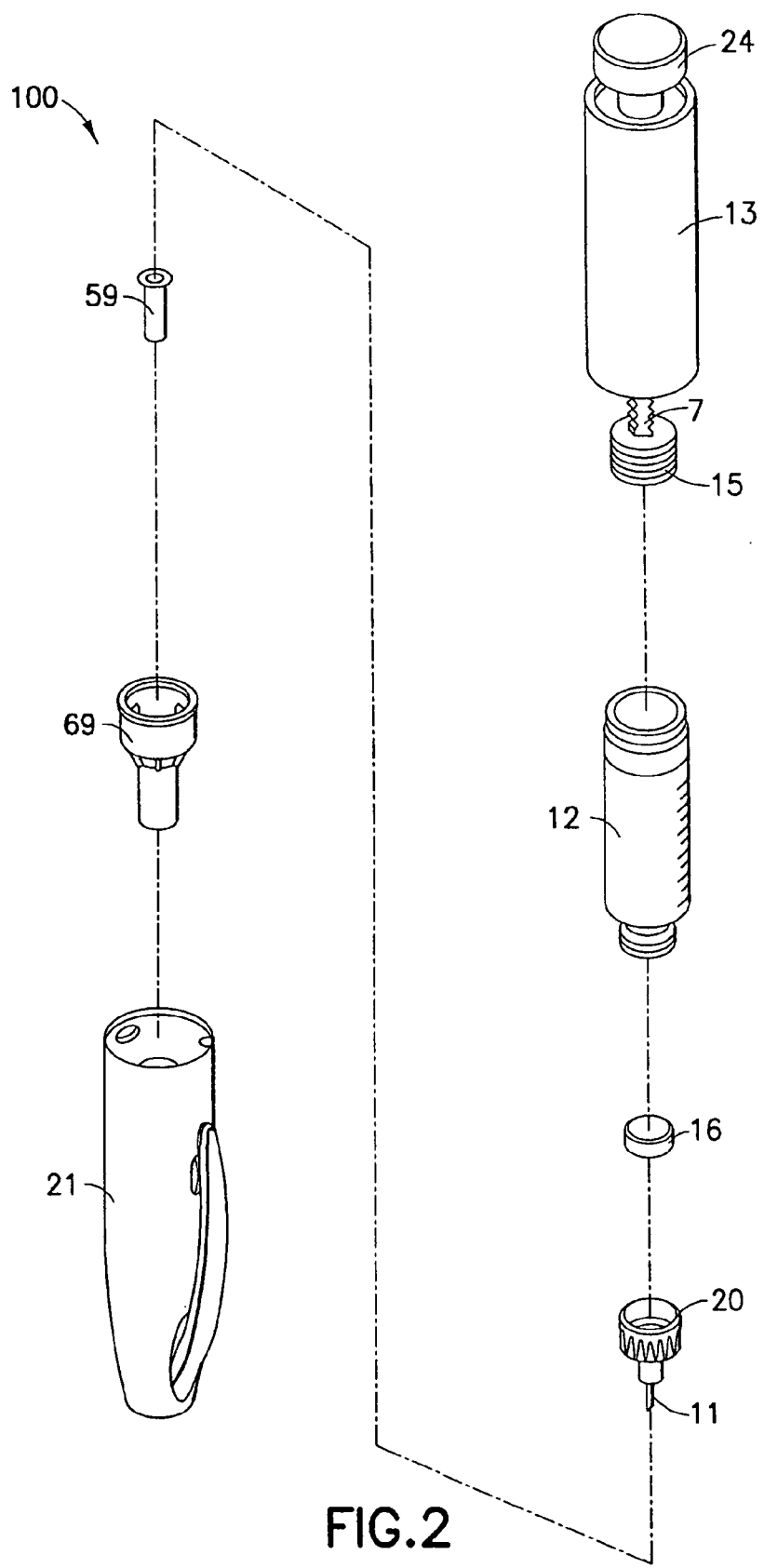
FIG. 2 is an exploded perspective view of the components of the drug delivery pen of FIG. 1.
Figure 3:
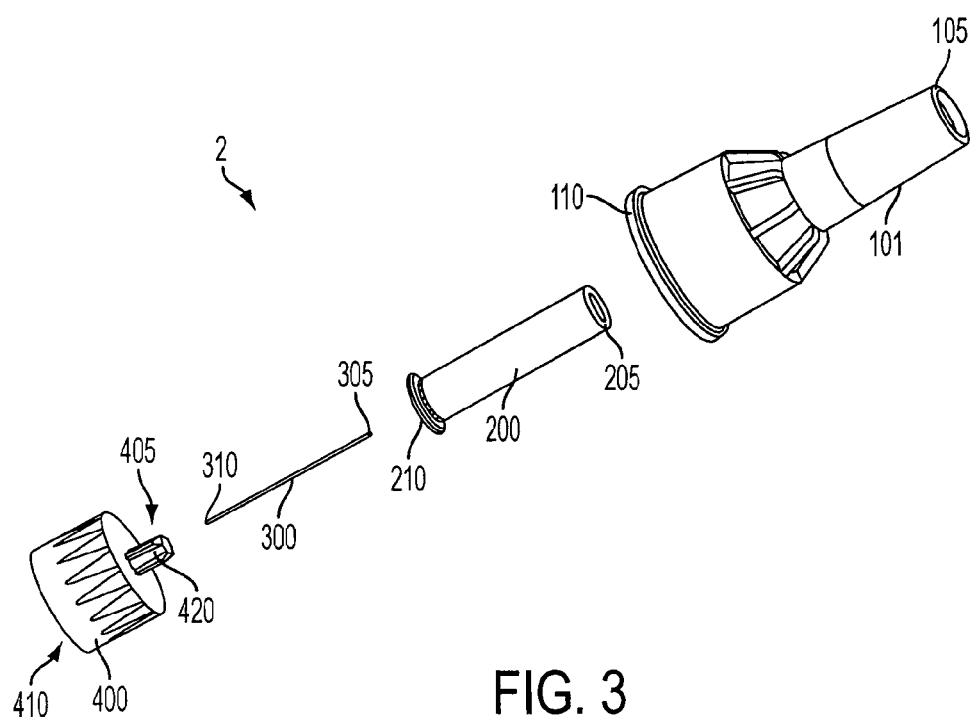
FIG. 3 is an exploded perspective view of a needle assembly for a drug delivery pen.
Figure 4:
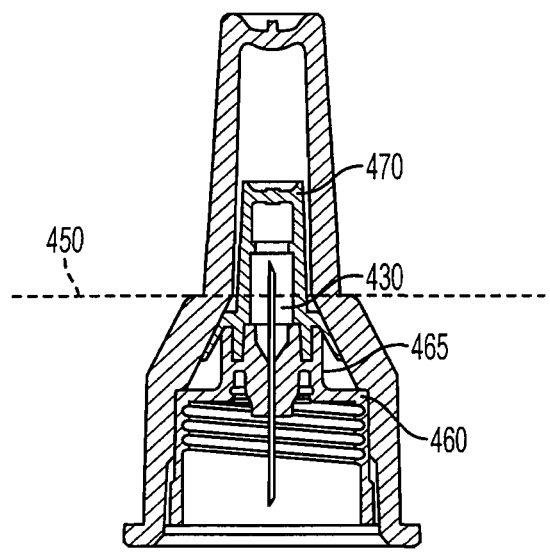
FIG. 4 is a cross-sectional view of the pen needle hub assembly of FIG. 3 in an as-manufactured state.
Figure 5:
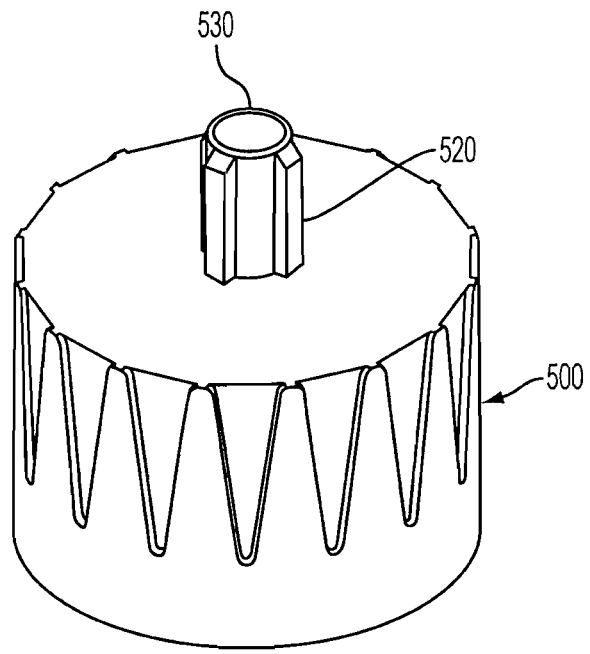
FIG. 5 is a perspective view of an existing hub for a pen needle assembly.

The following description and details of exemplary embodiments of the present invention, while generally disclosed in a typical drug delivery pen, as shown in FIGS. 1 and 2, could more broadly apply to a needle and hub assembly for use in conjunction with, or incorporated onto, other injection devices such as syringes, infusion devices and any other needle-containing devices in which such features are desirable.

In the exemplary embodiments of the present invention, a hub has an increased surface area that contacts a patient's skin during an injection to reduce the pressure exerted against the patient's skin during the injection, thereby increasing the comfort of the patient. Additionally, the increased contact surface area provides a more stable injection surface during injection, particularly when using cannulas having shorter lengths.

Figure 6A:
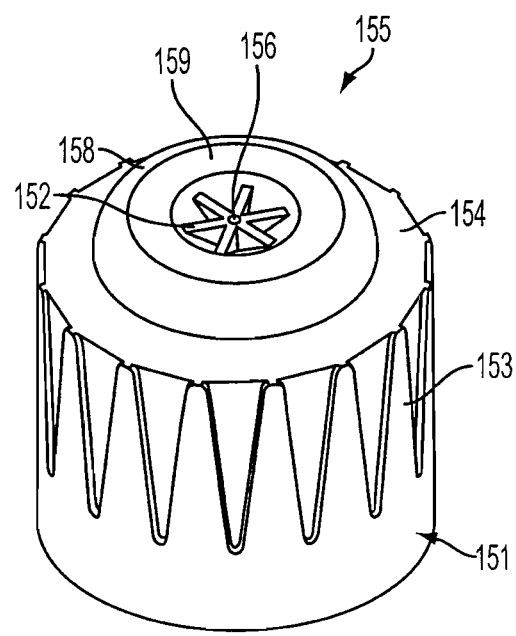
FIGS. 6A to 6C are perspective views of a hub for a pen needle assembly according a first exemplary embodiment of the present invention.
Figure 6B:
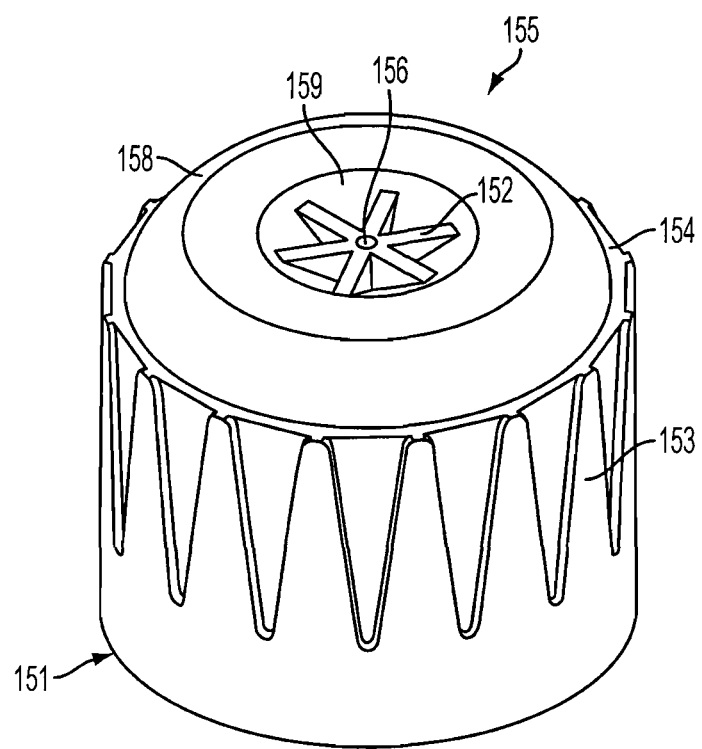
Figure 6C:
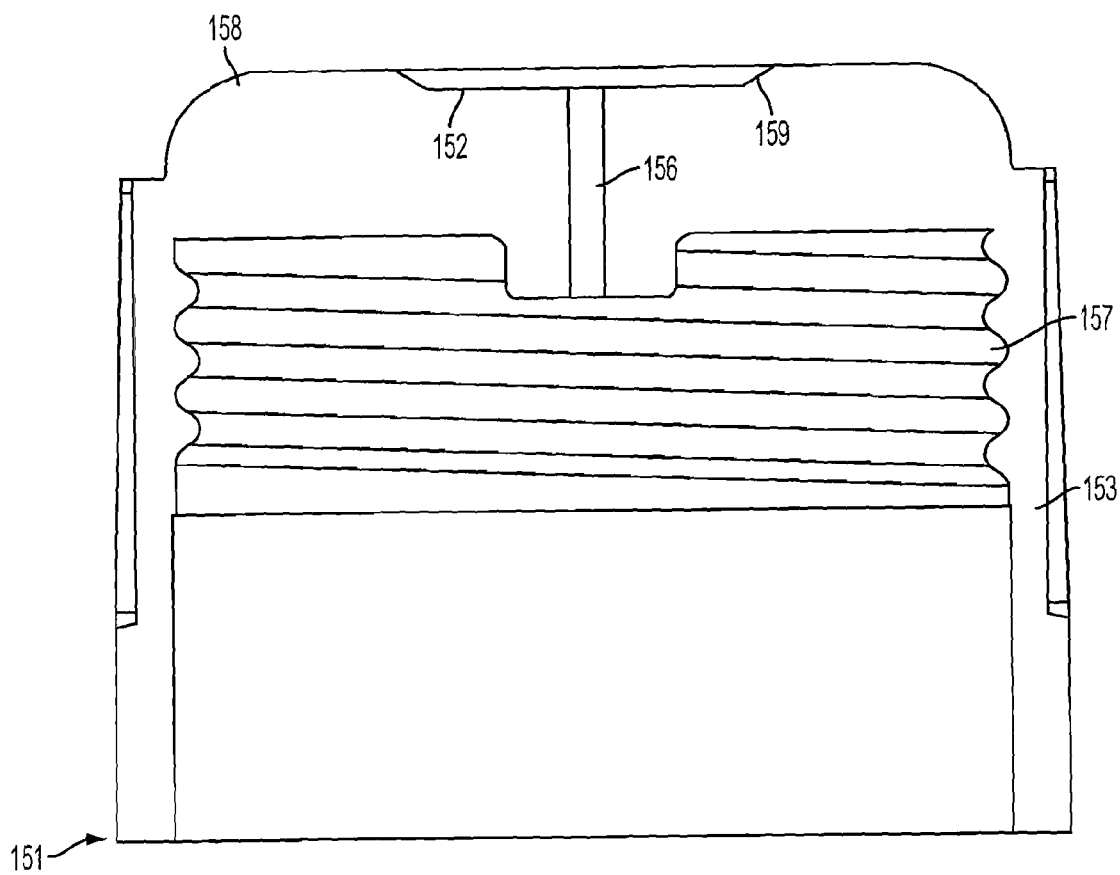

A hub 151, as shown in FIGS. 6A-6C, has a substantially cylindrical body 153. A projection, or protrusion, 155 extends outwardly from a distal end 154 of the body 153 of the hub 151. An opening 156 in the projection 151 receives a cannula. The increased surface area at the distal end 158 of the protrusion reduces the pressure exerted against a patient's skin during cannula injection, thereby increasing the patient's comfort. Preferably, the hub 151 is made of plastic, such as polypropylene.

The adhesive for bonding the cannula to the hub 151 is disposed on the outer surface at the distal end 158 of the protrusion 155. The distal end 158 is preferably provided having a contour near its outer circumference that becomes substantially flat while approaching the inner portion 159. The inner portion 159 of the projection 151 slopes downwardly toward the opening 156, thereby facilitating movement of the adhesive to the opening. A plurality of ribs 152 are disposed in the inner portion 159 that increase the contact surface area between the adhesive and the hub 151. When the adhesive is cured, the inner portion 159 is substantially filled with the adhesive such that the distal end 158 of the projection 155 is substantially flush. By disposing the adhesive on the outer surface of the protrusion 155, the UV radiation used to cure the adhesive does not have to pass through the hub walls to irradiate the adhesive. Thus, the curing time for the adhesive is decreased. Furthermore, the contact area between the cannula adhesive and the hub 151 is also increased, thereby increasing the bond strength of the cannula adhesive with the hub 151. Corona, plasma or other surface treatment may be used with this or any other embodiment to increase the adhesive/hub bond strength.

FIGS. 6A and 6B are perspective views of a hub for a pen needle assembly according to a first exemplary embodiment of the present invention, and FIG. 6C is a cross-sectional view of the hub of FIGS. 6A and 6B taken along center line of a rib 152. The cross-sectional view of FIG. 6C shows the inner threads 157 of the hub 151 and shows the opening 156 extending through the distal end 158 for communication with an interior of the hub 151. However, in yet other embodiments of the present invention, the opening 156 may be modified as shown in FIG. 6D.

Figure 6D:
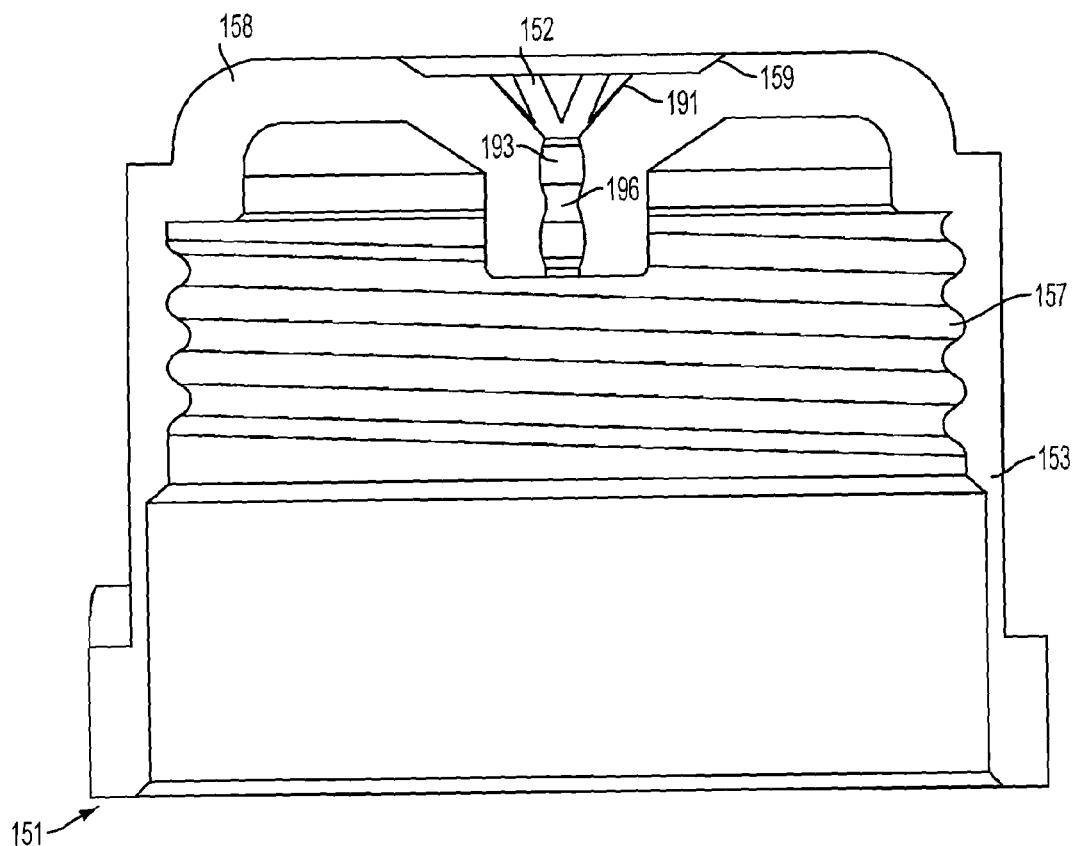
FIG. 6D is a perspective view of a hub for a pen needle assembly according to the first exemplary embodiment of the present invention and having additional adhesive spacing.

FIG. 6D is a perspective view of a hub for a pen needle assembly according to the first exemplary embodiment of the present invention and having additional adhesive spacing. Specifically, as shown in FIG. 6D, an opening 196 may be provided having one or more rings 193 or other feature to facilitate adhesive filling. These rings 193 may be used with any embodiment of the needle hub to improve the cannula/hub bond strength. Furthermore, the entrance of the opening 196 may be provided with a guide space or slope 191 by modifying the ribs 152 at a point immediately surrounding the opening 196. Such a guide space 191 may facilitate needle positioning by serving as a guide during assembly.

Figure 7A:
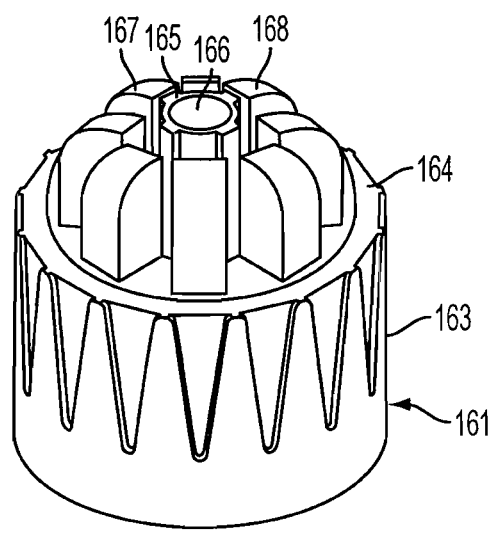
FIG. 7A is a perspective view of a hub for a pen needle assembly according a second exemplary embodiment of the present invention.
Figure 7B:
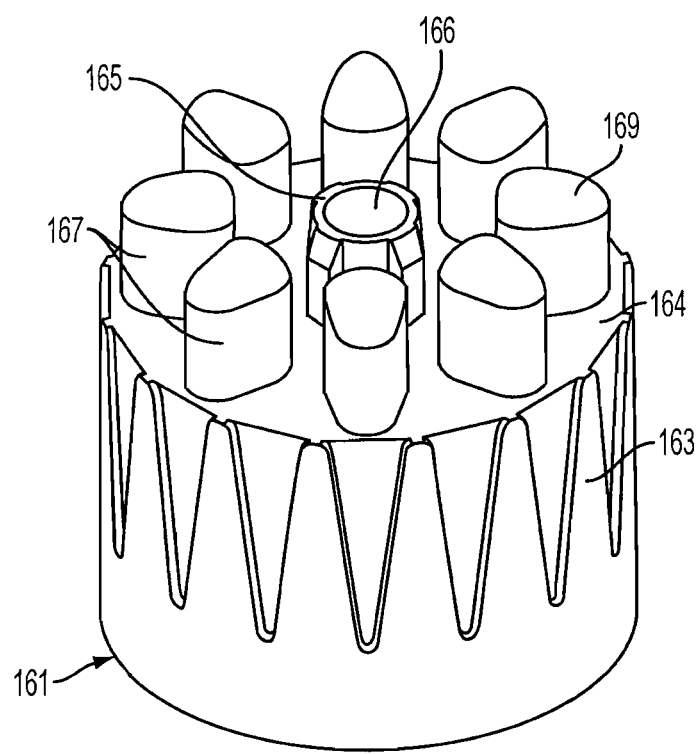
FIG. 7B is a perspective view of a hub for a pen needle assembly according to the second exemplary embodiment of the present invention and having additional contours for angle injections.

A hub 161, as shown in FIGS. 7A and 7B, has a substantially cylindrical body 163. A protrusion 165 extends outwardly from a distal end 164 of the body 163 of the hub 161. An opening 166 in the protrusion 165 receives a cannula. A plurality of projections 167 surround the protrusion 165. The distal ends 168 of the plurality of projections 167 form a substantially planar surface for contacting a patient's skin during injection. The distal ends 168 of the plurality of projections 167 are preferably flush with or extend beyond the distal end of the protrusion 165. The increased surface area provided by the distal ends 168 of the plurality of projections reduces the pressure exerted against a patient's skin during cannula injection, thereby increasing the patient's comfort. However, in yet other exemplary embodiments of the present invention, the distal ends of the plurality of projections 167 may be modified as shown in FIG. 7B.

FIG. 7B is a perspective view of a hub for a pen needle assembly according the second exemplary embodiment of the present invention and having additional contours for angle injections. In the exemplary embodiment shown in FIG. 7B, distal end 169 of the plurality of projections 167 are contoured, rounded and/or provided with a shape and radius to facilitate injections that may occur or be attempted at angles other than perpendicular to the skin surface, while maintaining the benefit of the increased surface area provided by the distal ends of the plurality of projections.

Figure 8A:
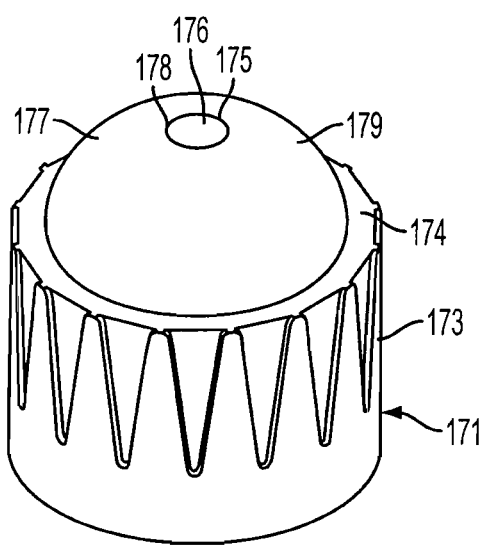
FIGS. 8A and 8B are perspective views of a hub for a pen needle assembly according a third exemplary embodiment of the present invention.
Figure 8B:
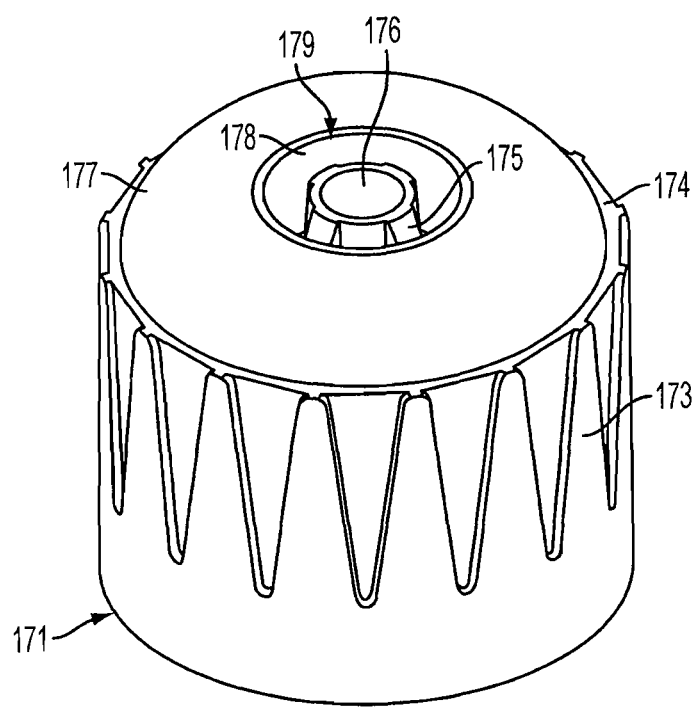
Figure 8C:
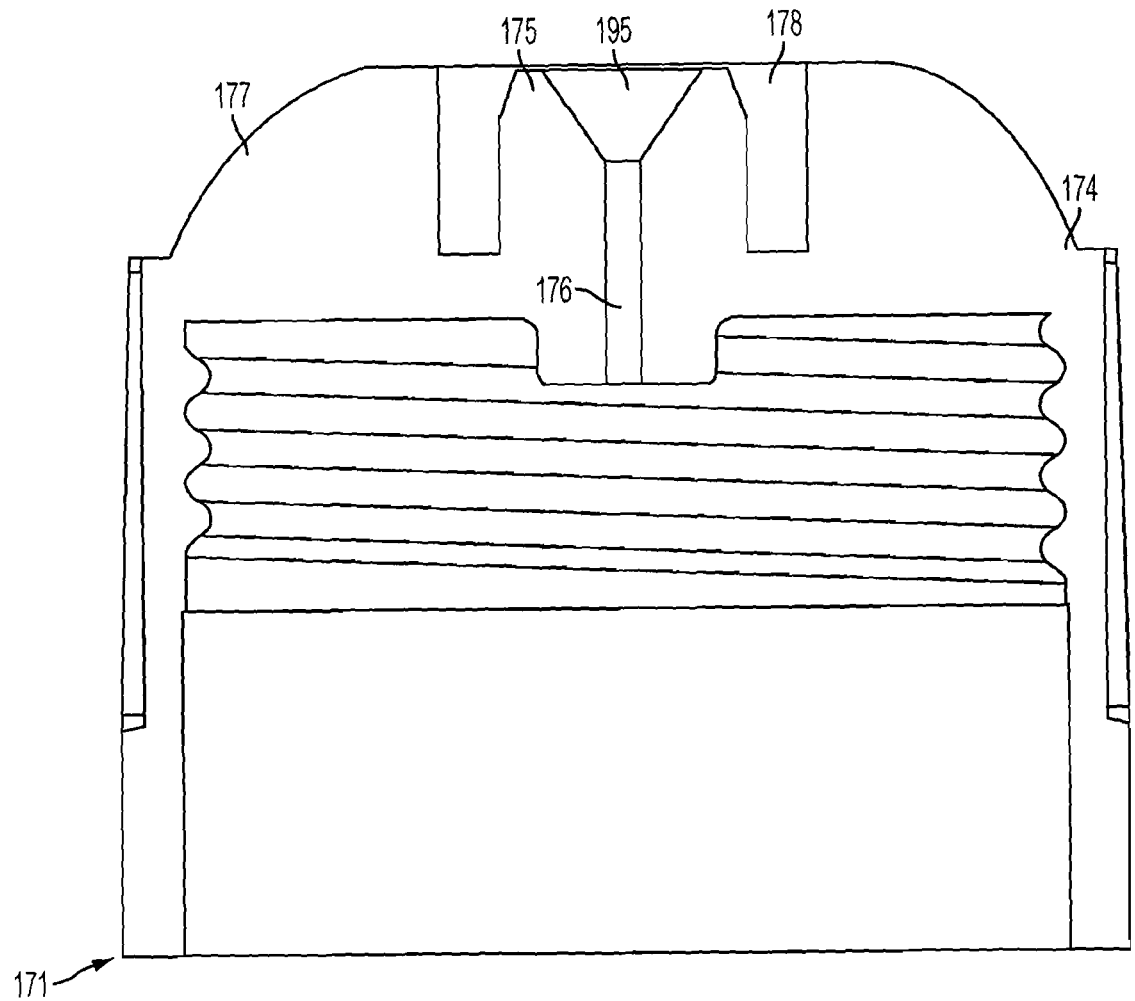
FIG. 8C is a cross-sectional view of a hub for a pen needle assembly according to the third exemplary embodiment of the present invention.

A hub 171, as shown in FIGS. 8A-8C, has a substantially cylindrical body 173. A protrusion 175 extends outwardly from a distal end 174 of the body 173 of the hub 171. An opening 176 in the protrusion 175 receives a cannula. A substantially hemispherical projection 177 extends outwardly from the distal end 174 of the hub 171. An opening 178 in the projection 177 is substantially flush with the distal end of the protrusion 175. The distal end 179 of the projection 177 is substantially planar for contacting a patient's skin during injection. The distal end 179 of the projection 177 is preferably flush with or extends beyond the distal end of the protrusion 175 (FIG. 8C). The increased surface area provided by the distal end 179 of the projection 177 reduces the pressure exerted against a patient's skin during cannula injection, thereby increasing the patient's comfort. The recessed ring 178 of the surface of the hub 171 may be used to facilitate attachment of a cannula shield. The recessed ring on the surface of the hub may also be used to facilitate manufacturing of the pen needle assembly by collecting adhesive that might overflow from the adhesive well at the center of the hub.

As shown in greater detail in FIG. 8C, the adhesive well 195 may be provided at or near the end of the protrusion 175. Furthermore, as noted above and more clearly shown in FIG. 8C, the distal end of the projection 177 is preferably substantially flush with or extends slightly beyond the distal end of the protrusion 175. Further, inner threads of the hub 171 are shown.

Figure 9A:
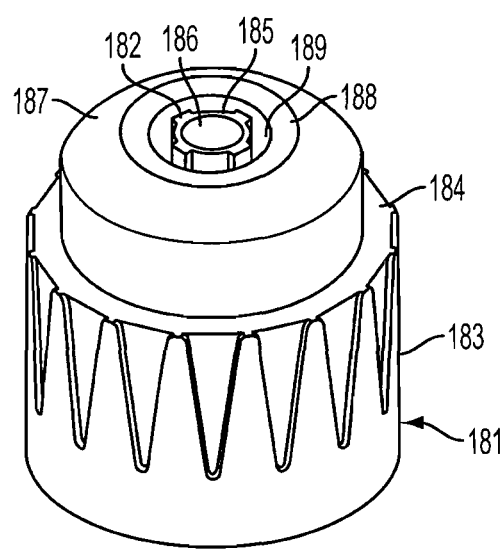
FIGS. 9A and 9B are perspective views of a hub for a pen needle assembly according a fourth exemplary embodiment of the present invention.
Figure 9B:
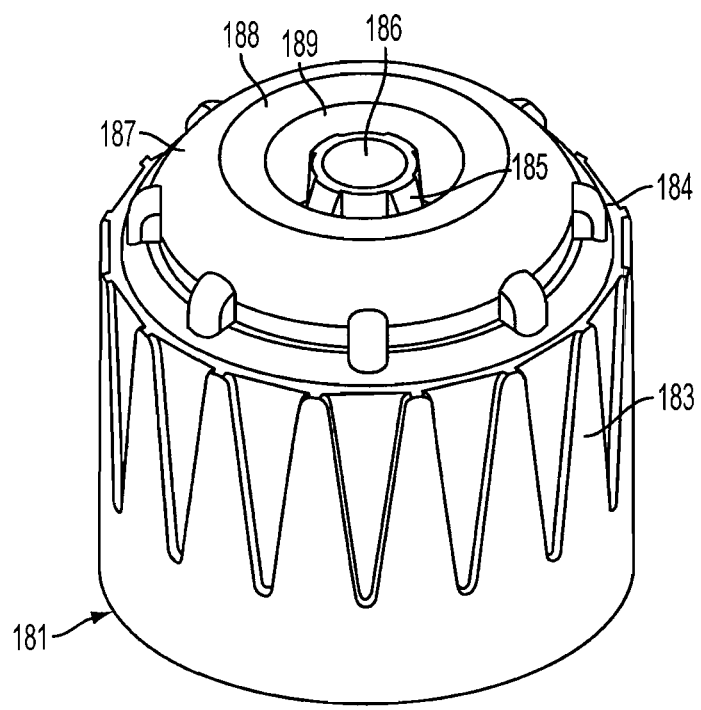
Figure 9C:
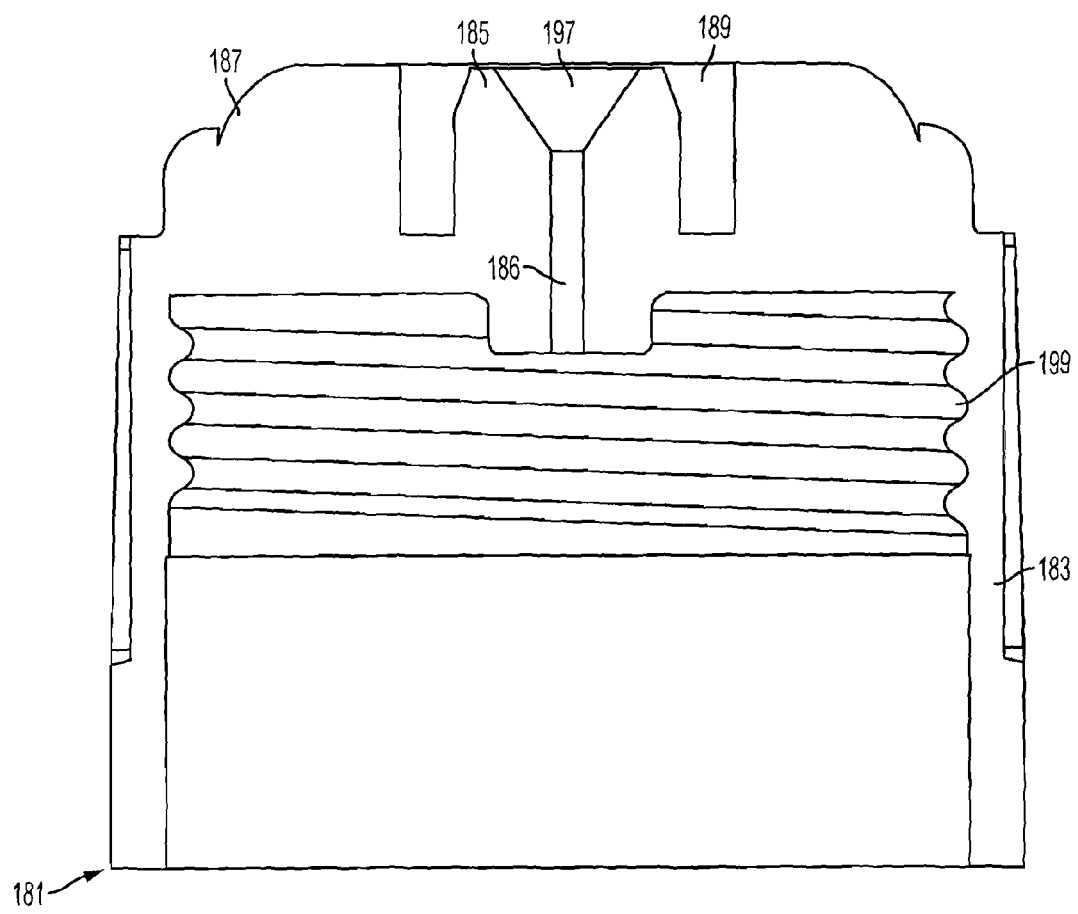
FIG. 9C is a cross-sectional view of a hub for a pen needle assembly according to the fourth exemplary embodiment of the present invention.

A hub 181, as shown in FIGS. 9A-9C, has a substantially cylindrical body 183. A protrusion 185 extends outwardly from a distal end 184 of the body 183 of the hub 181. An opening 186 in the protrusion 185 receives a cannula. A substantially spherical projection 187 extends outwardly from the distal end 184 of the hub 181. A distal surface 188 of the projection 187 is substantially flush with a distal end 182 of the protrusion 185. The distal surface 188 of the projection 187 is substantially planar for contacting a patient's skin during injection. The distal surface 188 of the projection 187 is preferably flush with or extends beyond the distal end 182 of the protrusion 185. An inner portion 189 of the projection 187 slopes inwardly and downwardly toward the protrusion 185 to form a valley, which is adapted to receive another member of the pen needle assembly, such as a shield. The increased surface area provided by the distal surface 188 of the projection 187 reduces the pressure exerted against a patient's skin during cannula injection, thereby increasing the patient's comfort.

As shown in greater detail in FIG. 9C, an adhesive well 197 may be provided at or near the end of the protrusion 185. Further, inner threads 199 of the hub 181 are shown.

Figure 10A:
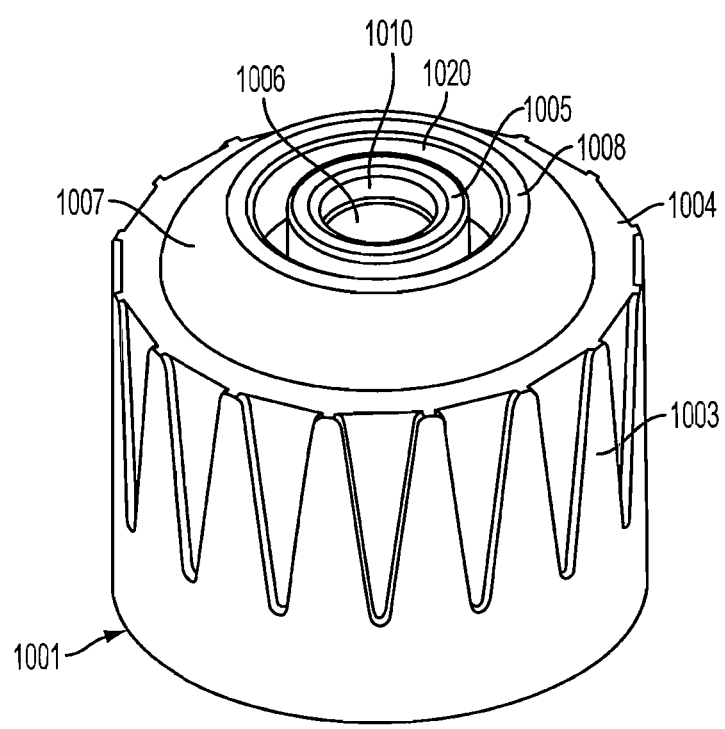
FIG. 10A is a perspective view of a hub for a pen needle assembly according to a fifth exemplary embodiment of the present invention.
Figure 10B:
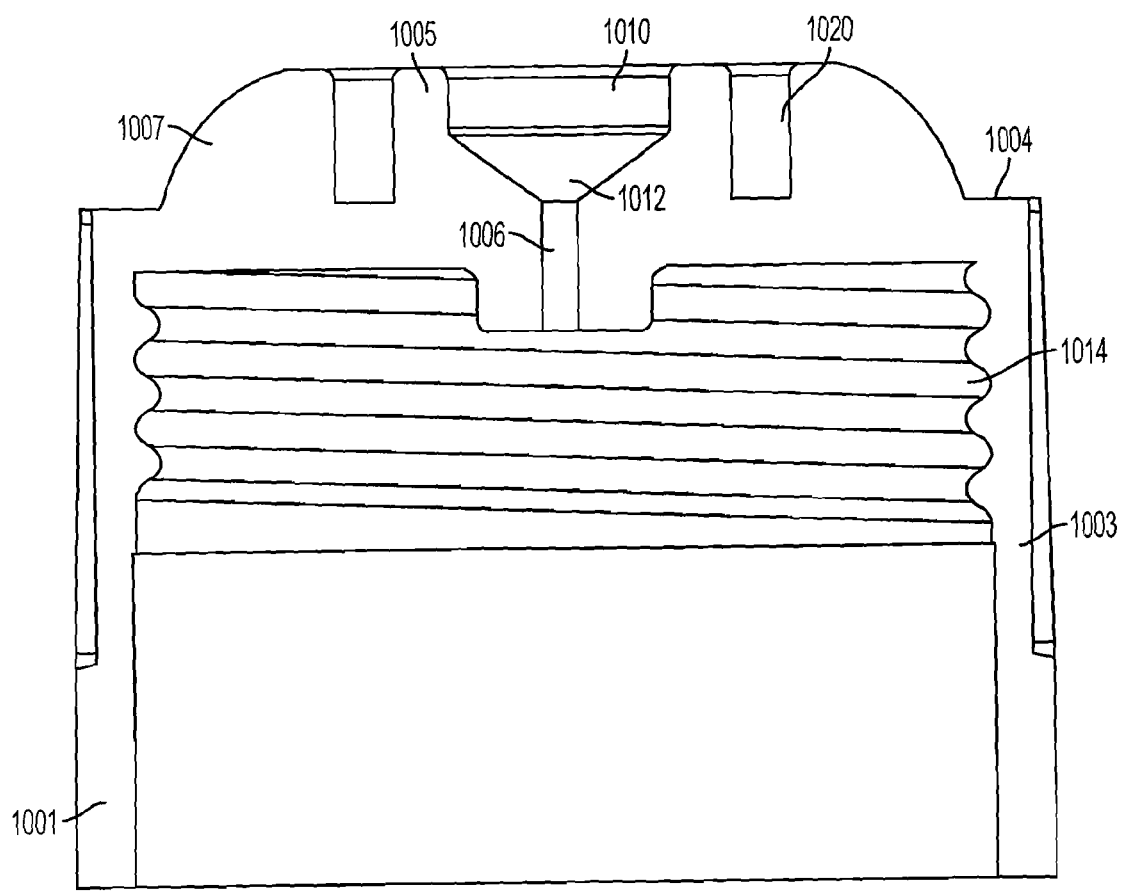
FIG. 10B is a cross-sectional view of a hub for a pen needle assembly according to the fifth exemplary embodiment of the present invention.

A hub 1001, as shown in FIGS. 10A-10B, has a substantially cylindrical body 1003. A protrusion 1005 extends outwardly from a distal end 1004 of the body 1003 of the hub 1001. An opening 1006 in the protrusion 1005 receives a cannula. A substantially spherical projection 1007 extends outwardly from the distal end 1004 of the hub 1001. A distal surface 1008 of the projection 1007 is substantially flush with a distal end of the protrusion 1005. The distal surface 1008 of the projection 1007 is substantially planar for contacting a patient's skin during injection. The distal surface 1008 of the projection 1007 is preferably flush with or extends beyond the distal end of the protrusion 1005.

The exemplary embodiment shown in FIG. 10A is formed having two concentric wells 1010 and 1020, with the inner well 1010 provided to capture excess adhesive and the outer well 1020 provided to receive and secure a shield, but are not limited thereto.

As shown in greater detail in FIG. 10B, an adhesive well 1012 may be provided at or near the end of the protrusion 1005. The adhesive well 1012 facilitates visual inspection of the amount of adhesive in the well by using a single top view inspection camera. The more adhesive in the well, the wider the circle of adhesive that is visible in a top-down view. Current inspection methods overfill the glue well and look for glue overflowing the hub protrusion. Further, inner threads 1014 of the hub 1001 are shown.

The foregoing embodiments and advantages are merely exemplary and are not to be construed as limiting the scope of the present invention. The description of exemplary embodiments of the present invention is intended to be illustrative, and not to limit the scope of the present invention. Various modifications, alternatives and variations will be apparent to those of ordinary skill in the art, and are intended to fall within the scope of the invention, as defined in the appended claims.

What is claimed is:

1. A hub assembly for an injection apparatus, comprising:
a body having a first end;
an outer projection extending outwardly from said first end of said body, said projection having a distal end having an outer circumference and an inner portion;
said body having an opening to receive cannula, said opening extending to an interior of said body;

a plurality of axially extending ribs disposed on said inner portion of said outer projection and extending radially inward from said outer projection to said opening;

said inner portion of said projection surrounding and sloping inwardly toward said opening, wherein an adhesive applied to said inner portion of said outer projection flows from said inner portion between said ribs and to said opening to secure the cannula;

a distal end of said outer circumference having a substantially flat planar axial face with a surface area for reducing the pressure exerted against a patient's skin during an injection; and said outer circumference having a curved portion extending between said first end of said body and said substantially flat planar axial face of said distal end of said outer circumference, said curved portion being curved in a longitudinal direction of said projection, said projection surrounding said opening and being spaced radially outward from said opening and cannula.

2. The hub assembly for an injection apparatus according to claim 1, wherein
a plurality of rings are formed in said opening to facilitate receipt of the adhesive.

3. The hub assembly for an injection apparatus according to claim 1, wherein
a distal end of said projection extends beyond said ribs and opening.

4. The hub assembly for an injection apparatus according to claim 1, wherein
said projection has a substantially flat planar distal end forming said axial face to facilitate injections substantially perpendicular to a skin surface.

5. The hub assembly for an injection apparatus according to claim 4, wherein
said projection has a curved, rounded surface extending between said flat planar distal end and said first end of said body to facilitate injections not perpendicular to a skin surface.

6. The hub assembly for an injection apparatus according to claim 1, wherein
a recessed ring is formed between said opening and said inner portion of said distal end of said projection.

7. The hub assembly for an injection apparatus according to claim 1, wherein
a distal end of said opening has an increased diameter to facilitate receipt of the adhesive.

8. The hub assembly for an injection apparatus according to claim 1, wherein
said body has a longitudinal center axis, and
said axial face of said distal end of said projection defines an annular surface extending radially between said outer portion and said inner portion and has a radial dimension greater than a radial dimension of said ribs.

9. The hub assembly for an injection apparatus according to claim 1, wherein
said ribs are recessed with respect to said axial face of said projection.

10. A hub assembly for an injection apparatus, comprising:
a body having a first end;
an inner protrusion extending outwardly from said first axial end of said body and having a substantially flat planar distal end, said distal end of said protrusion defining an axial face and being substantially continuous and equidistant from said first axial end of said body;
an opening in said distal end of said protrusion adapted to receive a cannula, said opening extending to an interior of said body; and
an outer projection spaced from and circumferentially surrounding said protrusion, said outer projection defined by a plurality of spaced-apart members spaced radially outward from said protrusion, a distal end of said members having a substantially flat planar axial face to form a distal end of said outer projection having an increased surface area relative to said axial face of said protrusion, thereby reducing the pressure exerted against a patient's skin during an injection, said distal end of said projection extending axially beyond said distal end of said protrusion and having curved outer surface extending between said substantially flat planar axial face and said first end of said body.

11. The hub assembly for an injection apparatus according to claim 10, wherein
said plurality of members extend beyond said distal end of said protrusion and said opening.

12. The hub assembly for an injection apparatus according to claim 10, wherein
a well is formed between said projection and said protrusion to facilitate receipt of an adhesive to secure the cannula to said hub assembly.

13. The hub assembly for an injection apparatus according to claim 10, wherein
a recessed ring is formed in said projection.

14. The hub assembly for an injection apparatus according to claim 10, wherein
ends of said plurality of members have a substantially flat, planar distal end to facilitate injections substantially perpendicular to a skin surface.

15. The hub assembly for an injection apparatus according to claim 14, wherein
each of said plurality of members have a rounded radially facing outer surface extending between said flat planar distal end of said member and said first axial end of said body to facilitate injections not perpendicular to a skin surface.

16. The hub assembly for an injection apparatus according to claim 10, wherein
the flat planar distal end of said projection is equidistant from said first axial end of said body to facilitate contacting the patient's skin during the injection.

17. The hub assembly for an injection apparatus according to claim 10, wherein
said projection is spaced inwardly from an outer edge of said first end of said body.

* * * * *